(12) United States Patent
Frahling et al.

(10) Patent No.: US 9,023,333 B2
(45) Date of Patent: May 5, 2015

(54) METHOD OF USING SHAPED ARTICLES TO APPLY A SCAFFOLD-FORMING AGENT TO AN EXTERNAL SKIN AND/OR HAIR SURFACE OF A HUMAN OR AN ANIMAL

(76) Inventors: Stefan Frahling, Billerbeck (DE); Ralf Malessa, Essen (DE)

( * ) Notice: Subject to any disclaimer, the term of this patent is extended or adjusted under 35 U.S.C. 154(b) by 14 days.

(21) Appl. No.: 10/531,346

(22) PCT Filed: Sep. 30, 2003

(86) PCT No.: PCT/EP03/10853
§ 371 (c)(1),
(2), (4) Date: Apr. 15, 2005

(87) PCT Pub. No.: WO2004/035023
PCT Pub. Date: Apr. 29, 2004

(65) Prior Publication Data
US 2005/0281849 A1 Dec. 22, 2005

(30) Foreign Application Priority Data

Oct. 16, 2002 (DE) .................. 102 48 314
Apr. 17, 2003 (DE) .................. 103 17 982

(51) Int. Cl.
| | | |
|---|---|---|
| A61K 31/74 | (2006.01) | |
| A61K 8/02 | (2006.01) | |
| A61K 31/715 | (2006.01) | |
| A61K 47/00 | (2006.01) | |
| A61Q 5/00 | (2006.01) | |
| A61K 8/73 | (2006.01) | |
| A61Q 19/00 | (2006.01) | |
| C08L 5/04 | (2006.01) | |

(52) U.S. Cl.
CPC ... *A61Q 5/00* (2013.01); *A61K 8/02* (2013.01); *A61K 8/733* (2013.01); *A61Q 19/00* (2013.01); *C08L 5/04* (2013.01)

(58) Field of Classification Search
USPC .......................................... 424/401, 744, 451
IPC ....................................................... A61K 7/48
See application file for complete search history.

(56) References Cited

U.S. PATENT DOCUMENTS

| | | | |
|---|---|---|---|
| 4,758,598 A | 7/1988 | Gregory | |
| 5,132,295 A | 7/1992 | Balz et al. | |
| 5,384,129 A | 1/1995 | Wunderlich et al. | |
| 5,387,415 A | 2/1995 | Wunderlich et al. | |
| 5,401,502 A | 3/1995 | Wunderlich et al. | |
| 5,405,616 A | 4/1995 | Wunderlich et al. | |
| 5,578,307 A * | 11/1996 | Wunderlich et al. | 424/744 |
| 5,622,693 A | 4/1997 | Funatsu | |
| 6,269,817 B1 * | 8/2001 | Nagashima et al. | 128/898 |
| 6,497,887 B1 * | 12/2002 | Zecchino et al. | 424/401 |
| 2002/0068683 A1 * | 6/2002 | Kojima | 508/110 |

FOREIGN PATENT DOCUMENTS

| | | | | |
|---|---|---|---|---|
| DE | 4328329 A1 | 3/1994 | | |
| EP | 0 888 769 | * 1/1999 | ............... | A61K 7/48 |
| EP | 0888769 A1 | 7/1999 | | |
| JP | 59-108045 | 6/1984 | | |
| JP | 61-022006 | 1/1986 | | |
| JP | H02-196795 | 8/1990 | | |
| JP | 7-502735 | 3/1995 | | |
| JP | 10-025231 | 1/1998 | | |
| JP | 2001-48746 | 2/2001 | | |
| JP | 2002-275048 | 9/2002 | | |
| WO | 89/12407 | 12/1989 | | |
| WO | 93/13754 | 7/1993 | | |
| WO | 96/23817 | 8/1996 | | |

OTHER PUBLICATIONS

Hawley's Condensed Chemical Dictionary, 13th Ed.; p. 288 (Collagen).*
The Handbook of Pharmaceutical Excipients (1988); p. 5; Alginic acid.*
Machine Translation of DE 43 28 329 (1994) provided; downloaded May 17, 2013.*
Hawley's Condensed Chemical Dictionary, 13th Ed.; p. 288 (Collagen); published Sep. 19, 1997.*
Partial English Translation of JP H02-196795, 2 pages.
Partial English Translation of JP 2001-48746, 11 pages.
Patent Abstracts of Japan, JP 61-022006, 1 page.
Partial English Translation of JP 2002-275048, 5 pages.
Patent Abstracts of Japan, JP 59-108045, 1 page.
Partial English Translation of JP 10-025231, 8 pages.
Lapasin et al., "Rheology of Industrial Polysaccharides, Theory and Applications," copyright 1995, 1999 by Aspen Publishers, Inc., pp. 273-281.
Young et al., "Introduction to Polymers, Second Edition," Library of Congress Cataloging-in-Publication Data, copyright 1991 Chapman & Hall, pp. 194-204.
Van Krevelen, "Additive Molar Functions Connected With Molecular Mobility (Viscometric and Rheological Properties of Polymers)," Computational Modeling of Polymers, Library of Congress Cataloging-in-Publication Data, copyright 1992 by Marcel Dekker, Inc., p. 108.
Albert Einstein, Investigations on the Theory of the Brownian Movement, "Movement of Small Particles," R. Fürth (editor), Dover Publications, pp. 11-13, Originally published in 1926.
Kuntz, "Special Effects With Gums," Food Product Design, Dec. 1999, nine pages.
Flink et al. "A Novel Method for Immobilization of Yeast Cells in Alginate Gels of Various Shapes by Internal Liberation of Ca-IONS," Biotechnology Letters, vol. 7, No. 10, 1985, pp. 765-768.

* cited by examiner

*Primary Examiner* — Jeffrey T Palenik
(74) *Attorney, Agent, or Firm* — Fanelli Haag PLLC

(57) ABSTRACT

The invention relates to the use of a shaped article containing at least one skeleton-forming agent, proteins being excepted, optionally one or more active substances and also optionally one or more auxiliary substances for the purpose of external application, to a process for producing the stated shaped articles, and also to novel shaped articles.

20 Claims, No Drawings

METHOD OF USING SHAPED ARTICLES TO APPLY A SCAFFOLD-FORMING AGENT TO AN EXTERNAL SKIN AND/OR HAIR SURFACE OF A HUMAN OR AN ANIMAL

The invention relates to the use of a shaped article containing at least one skeleton-forming agent, proteins being excepted, optionally one or more active substances and also optionally one or more auxiliary substances for the purpose of external application, to a process for producing the stated shaped articles, and also to novel shaped articles.

In German printed patent specifications DE 42 01 172, DE 42 01 173 and DE 42 01 179, pellets for pharmaceutical or cosmetic application are described which comprise skeleton-forming agents based on proteins. The pellets serve, in particular, for the production of oral medicinal formulations. The pellets are produced by dispersions consisting of the proteinic skeleton-forming agents and optionally of cosmetic or pharmaceutical active substances being instilled into intensely cold inert liquids, preferably liquid nitrogen, and by the frozen pellets subsequently being separated and freeze-dried. However, in order to form pellets under these conditions the presence of proteinic skeleton-forming agents, in particular collagen or collagen derivatives, is required, since only the stated proteinic skeleton-forming agents are able to form stable pellets under these conditions. This is presumably connected with the special intermolecular interactions of the protein molecules.

The size of the pellets that are produced in accordance with the cited German printed patent specifications is specified in the general part of the descriptions at 0.2 mm to 12 mm. In the Examples, however, the maximum size that is achieved amounts to only 4 mm. In this connection it is a question of an average size—that is to say, the pellets are subject to more or less considerable fluctuations in size.

In particular for external cosmetic application, however, relatively large shaped articles of uniform shape and size are preferred. The consumer is able to handle such shaped articles easily. As a rule, powders, or alternatively small pellets or irregularly formed shaped articles, are unsuitable for these purposes. The aim is to prepare shaped articles of such a size that permit a dosage form to be used for each application. In addition, larger shaped articles, which may be coloured, for example, also convey a better aesthetic impression.

In addition, in some cases the application of proteinic skeleton-forming agents is not preferred. For instance, some consumers are increasingly preferring the application of purely vegetable products, particularly in the cosmetic field. The reasons for this have resulted from, inter alia, fundamental ethical considerations.

Moreover, the reprocessing of proteins requires, as a rule, complicated reconditioning steps. Furthermore, the properties of the proteinic skeleton-forming agents in the case of external application on the skin are in many cases too limited in their range, since they are always composed of the same amino acids.

Therefore there is increasingly a desire for cosmetic or pharmaceutical moulded formulations, in particular shaped articles for the purpose of external application, that are not protein-based. However, if it is desired to process vegetable-based skeleton-forming agents, such as alginates for example, in accordance with the process that is used in the aforementioned printed patent specifications, then it is surprisingly discovered that no shaped articles having regular shapes, in particular of sufficient size and with sufficient solubility such as are required for external application, can be produced in this way.

Numerous publications are concerned with the production of oral formulations, the production of which involves a freeze-drying step. For instance, compositions are known from EP-A-0 352 190 consisting of solid and porous unit forms which comprise microparticles and nanoparticles. These compositions are produced, inter alia, in such a way that pastes are charged into cavities of a mould and subsequently a lyophilisation is carried out. The object as stated in EP-A-0 352 190 consisted in finding oral formulations with a masking of taste that dissolve rapidly in water. A topical application of the formulations is not mentioned. Similarly, EP-A-0 399 902 discloses formulations produced by freeze drying which likewise serve for the preparation of taste-masked, rapidly soluble medicinal formulations. Formulations produced by freeze drying which likewise serve exclusively for oral application are known from U.S. Pat. No. 4,758,598. Soluble excipient materials for the administration of medicaments for oral application are known from U.S. Pat. No. 4,079,018. Administration systems with controlled release for oral administration are described in U.S. Pat. No. 4,695,463. Furthermore, freeze-dried compositions are known from EP-A-0 412 449, which, however, do not exhibit a regular geometry. None of the above prior-art documents, however, discloses the possibility of the production of relatively large-sized, regular shaped articles that dissolve readily in the course of external application on the skin and are capable of acting as active-substance carriers.

The object of the present invention consequently consisted in making available for external application a novel use of shaped articles containing active substances and comprising skeleton-forming agents that are not based on proteins. These shaped articles should be relatively large, should exhibit sufficient cohesion, that is to say, mechanical strength, should be regularly shaped, should dissolve readily in the course of application on the skin, and should result in a pleasant application sensation. Moreover, these shaped articles should be suitable to receive various active substances, such as, in particular, cosmetic active substances and therapeutic or pharmaceutical active substances, and to act as carriers for such substances.

The invention consequently provides the use of a shaped article containing at least one skeleton-forming agent, proteins being excepted, optionally one or more active substances and also optionally one or more auxiliary substances for the purpose of external application.

A "shaped article" in the sense of the invention is to be understood to mean a regularly shaped geometrical body; for example, in particular, spheres, cuboids, pyramids, stars, but also shaped articles modelled on natural shapes, such as, for example, those in the form of animals such as, for example, marine animals such as starfish, for example, seafood such as mussels etc., plants and parts of plants, such as leaves etc. All these shapes are available in accordance with the process for producing the shaped articles that are used in accordance with the invention, which is described further below. A plurality of the stated shaped articles in a container is also encompassed in accordance with the invention. It may also be a question of mixtures of shaped articles having various geometries. The shaped articles may be individually packed. However, particularly in the cosmetic application, a plurality of the shaped articles are preferably present in a container, in contact alongside one another.

The volumes of the shaped articles that are used are not restricted as such by reason of the process for their production. The volumes expediently amount to at least approximately 0.1 cm$^3$, preferably 0.3 cm$^3$, more preferably at least approximately 0.5 cm$^3$, still more preferably at least approximately 0.8 cm³. The volumes that are used are expediently restricted in the upward direction to up to approximately 6 cm³, preferably up to approximately 5 cm³, more preferably up to approximately 4 cm³. The size of the shaped articles is determined, inter alia, by the site of external application of the shaped articles. For instance, application on relatively large areas of the body or on the hair (for example, direct application of the moistened shaped articles on the back etc., or use as a bath additive) makes the use of relatively large shaped articles possible, whereas smaller shaped articles are preferred in the case of application on smaller parts of the body (for example, the cheek etc.).

The diameter of a shaped article (maximum spacing between two points in a shaped article of arbitrary geometry) expediently amounts to at least approximately 3 mm, preferably at least approximately 5 mm, more preferably at least approximately 7 mm, still more preferably at least approximately 8 mm, up to, expediently, approximately 60 mm, preferably approximately 50 mm, more preferably approximately 40 mm, still more preferably approximately 30 mm.

A particularly preferred shaped article exhibits a substantially spherical geometry, the diameter of the sphere being between 3 mm and 30 mm, preferably between 5 mm and 20 mm, more preferably between 7 mm and 15 mm, still more preferably between 8 mm and 13 mm.

The shaped article that is used in accordance with the invention contains at least one skeleton-forming agent, proteins being excepted. In the case of the skeleton-forming agent it is generally a question of so-called hydrocolloids—that is to say, (partially) water-soluble, natural or synthetic polymers that form gels or viscous solutions in aqueous systems. The skeleton-forming agents are expediently selected from polysaccharides or synthetic polymers. The skeleton-forming agent is preferably selected from the group of the polysaccharides. Polysaccharides include, for example, homoglycans or heteroglycans, such as, for example, alginates, especially sodium alginate, carrageenan, pectins, tragacanth, guar gum, carob-bean flour, agar, gum arabic, xanthan gum, natural and modified starches, dextrans, dextrin, maltodextrins, chitosan, glucans such as β-1,3-glucan, β-1,4-glucan, such as cellulose, mucopolysaccharides, such as hyaluronic acid etc. Synthetic polymers include, for example: cellulose ethers, polyvinyl alcohol, polyvinyl pyrrolidone, synthetic cellulose derivatives, such as methylcellulose, carboxycellulose, carboxymethylcellulose, cellulose esters, cellulose ethers, such as hydroxypropylcellulose, polyacrylic acid, polymethacrylic acid, poly(methyl methacrylate) (PMMA), polymethacrylate (PMA), polyethylene glycols etc. Mixtures of several skeleton-forming agents may also be used. Particularly preferred in accordance with the invention are alginates, sodium alginate being particularly preferred. Preferred are low-viscosity skeleton-forming agents, in particular calcium-free sodium alginates (sodium alginate with a calcium content <3 wt. %, more preferably <2 wt. %, still more preferably <1.5 wt. %), that is to say, those skeleton-forming agents which preferably have a viscosity of less than 2000 mPa.s, still more preferably less than 1000 mPa.s, most preferably less than 100 mPa.s (i.e. a solution of 1 g of the skeleton-forming agent in 99 ml of distilled water (1% solution w/w) at 20° C. and at a pH value of 6-8 has a viscosity of, respectively, less than 2000 mPa.s, less than 1000 mPa.s, less than 100 mPa.s). The use of low-viscosity skeleton-forming agents such as sodium alginate is, on the one hand, preferred, owing to the manner of preparation; on the other hand, the application of such low-viscosity skeleton-forming agents results in readier solubility of the formulation or, in the case of addition of water, in a higher rate of disintegration or rate of dissolution and hence in readier distributability on the skin. In particular, the use of low-viscosity types of alginate can result in a greater rate of dissolution of the shaped articles that are used in accordance with the invention.

The polysaccharides that are preferably used as skeleton-forming agents in accordance with the invention expediently have average molar masses of approximately $10^3$ up to approximately $10^8$, preferably approximately $10^4$ to $10^7$.

The skeleton-forming agents are skin-compatible and, in the case of application on the skin, preferably result in the formation of a film that has a protective function.

With a view to clarification, it ought also to be mentioned that the wording "skeleton-forming agents, proteins being excepted" in the sense of the invention does not exclude the presence of protein-based active substances, such as enzymes, hormones etc.

The shaped articles that are used in accordance with the invention optionally contain one or more active substances, preferably at least one active substance. Active substances include, in particular, cosmetic or therapeutic or, to be more exact, pharmaceutical active substances that are suitable for external application. The shaped article that is used in accordance with the invention preferably contains at least one cosmetic and/or pharmaceutical active substance. Accordingly, in the case of the shaped articles that are used in accordance with the invention it is preferably a question of cosmetic or therapeutic agents. Cosmetic shaped articles or, to be more exact, shaped articles in the sense of the invention that have been produced using cosmetic active substances are essentially agents in the sense of the Lebensmittel- und Bedarfsgegenständegesetz (LMBG) [=German Foodstuffs and Commodities Act], that is to say, substances or preparations derived from substances that are intended to be applied externally on humans for the purpose of cleansing, grooming, or for the purpose of influencing appearance or body odour, or for the purpose of conveying impressions of odours, unless they are predominantly intended for relieving or eliminating diseases, ailments, physical defects or pathological complaints. In this sense, in the case of the cosmetic shaped articles that are used in accordance with the invention it is a question of, for example, bath preparations, skin-washing and skin-cleansing agents, skin-care products, in particular skin-care products for the face, eye cosmetics, lip-care products, nail-care products, foot-care products, hair-care products, in particular shampoos, hair-conditioning agents, hair conditioners etc., light-screening agents, tanning products, depigmentation agents, deodorants, antihydrotics, hair-removers, insect-repellents etc., or such products in combination.

Examples of cosmetically effective compounds, optionally also, for example, of dermatological, therapeutically effective compounds, include: anti-acne agents, antimicrobial agents, antiperspirants, astringent agents, deodorising agents, depilatories, conditioning agents for the skin, skin-smoothing agents, agents for increasing the hydration of the skin, such as, for example, glycerin or urea, sun-screening agents, keratolytics, radical-interceptors for free radicals, anti-seborrhoeics, anti-dandruff agents, antiseptic active substances, active substances for treating the symptoms of ageing of the skin and/or agents that modulate the differentiation and/or proliferation and/or pigmentation of the skin, vitamins such as vitamin C, active substances with irritant side-effect, such as α-hydroxy acids, β-hydroxy acids, α-keto acids, β-keto acids, retinoids (retinol, retinal, retinic acid), anthralins (dioxyanthranol), anthranoids, peroxides (in particular, benzoyl peroxide), minoxidil, lithium salts, antimetabolites, vitamin D and its derivatives; catechols, flavonoids, ceramides, fatty substances, such as mineral oils, such as paraffin oils or Vaseline oils, silicone oils, vegetable oils such as coconut oil, sweet-almond oil, apricot oil, corn oil, jojoba oil, olive oil, avocado oil, sesame oil, palm oil, eucalyptus oil, rosemary oil, lavender oil, pine oil, thyme oil, mint oil, cardamom oil, orange-blossom oil, soybean oil, bran oil, rice oil, rapeseed oil and castor oil, wheat-germ oil and vitamin E isolated therefrom, evening-primrose oil, vegetable lecithins (e.g. soybean lecithin), sphingolipids/ceramides isolated from plants, animal oils or fats, such as tallow, lanolin, butyric oil, fatty-acid esters, esters of fatty alcohols, and waxes with a melting-point corresponding to the temperature of the skin (animal waxes such as beeswax, carnauba wax and candelilla wax, mineral waxes such as microcrystalline waxes, and synthetic waxes such as polyethylene waxes or silicone waxes), as well as all oils that are suitable for cosmetic purposes, such as, for example, those mentioned in the CFTA treatise entitled Cosmetic Ingredient Handbook, $1^{st}$ Edition, 1988, The Cosmetic, Toiletry and Fragrance Association, Inc., Washington, polyunsaturated fatty acids, essential fatty acids (e.g. γ-linolenic acid), enzymes, coenzymes, enzyme inhibitors, hydrating agents, skin-soothing agents, detergents or foam-producing agents, and inorganic or synthetic matting fillers, abrasive agents.

Moreover, plant active-substance extracts or essences obtained therefrom or individual substances may be mentioned. Generally, the plant active-substance extract is selected, as a rule, from the group consisting of solid plant extracts, liquid plant extracts, hydrophilic plant extracts, lipophilic plant extracts, individual plant constituents, and also mixtures thereof, such as flavonoids and their aglycones: rutin, quercetin, diosmin, hyperoside, (neo)hesperidin, hesperitin, Ginkgo biloba (e.g. ginkgo flavone glycosides), Crataegus extract (e.g. oligomeric procyanidines), buckwheat (e.g. rutin), Sophora japonica (e.g. rutin), birch leaves (e.g. quercetin glycosides, hyperoside and rutin), elderflowers (e.g. rutin), lime blossoms (e.g. ethereal oil with quercetin and farnesol), hypericum oil (e.g. olive-oil essence), calendula, arnica (e.g. oleaginous essences of the flowers with ethereal oil, polar essences with flavonoids), melissa (e.g. flavones, ethereal oil); immunostimulants: Echinacea purpurea (e.g. alcoholic essences, fresh plant juice, pressed juice), Eleutherokokkus senticosus; alkaloids: rauwolfia (e.g. prajmaline), myrtle (e.g. vincamine); other phytopharmacons: aloe, horse chestnut (e.g. aescin), garlic (e.g. garlic oil), pineapple (e.g. bromelain), ginseng (e.g. ginsenosides), sow-thistle fruits (e.g. extract standardised with respect to silymarine), butcher's-broom root (e.g. ruscogenine), valerian (e.g. valepotriates, tct. valerianae), kava kava (e.g. kavalactones), hop flowers (e.g. hop bitters), extr. passiflorae, gentian (e.g. ethanolic extract), anthraquinone-containing tinctures, e.g. aloin-containing aloe-vera juice, pollen extract, algae extracts, liquorice-root extracts, palm extract, galphimia (e.g. mother tincture), mistletoe (e.g. aqueous ethanolic essence), phytosterols (e.g. β-sitosterol), mullen flowers (e.g. aqueous alcoholic extract), drosera (e.g. liqueur-wine extract, seabuckthorn fruits (e.g. juice obtained therefrom or sea-buckthorn oil), marshmallow root, primrose-root extract, fresh plant extracts from mallow, comfrey, ivy, horsetail, yarrow, ribwort (e.g. pressed juice), stinging nettle, celandine, parsley; plant extracts from Norolaena lobata, Tagetes lucida, Teeoma siems, Momordica charantia and aloe-vera extracts.

Preferred cosmetic active substances are natural and synthetic moisturising factors such as, for example, glycerin, urea and ceramides, skin-protecting agents, skin-lighteners, vitamins, antioxidants, so-called anti-ageing agents, anti-irritative agents, sun-screening agents, etc.

As distinct from the shaped articles described above, which are essentially used in the cosmetic field, in the case of the shaped articles that are used therapeutically (medicaments) it is a question of those which contain at least one pharmaceutical or therapeutic, in particular also dermatological, active substance and which in the sense of the Arzneimittelgesetz are intended, inter alia, to cure, relieve or prevent diseases, ailments, physical defects or pathological complaints. Such agents or active substances are intended for external application, in which case it may be a question of dermally active substances but also of transdermal active substances. They include, for example: agents for the treatment of skin diseases, externally applicable analgesics, e.g. dextropropoxyphene, pentazocine, pethidine, buprenorphine; antirheumatics/antiphlogistics (NSAR), e.g. indomethacin, diclofenac, naproxen, ketoprofen, ibuprofen, flurbiprofen, salicylic acid and salicylic-acid derivatives such as acetylsalicylic acid, oxicams; steroid hormones, e.g. betamethasone, dexamethosone, methylprednisolone, ethynyl estradiol, medroergotamine, dihydroergotoxine; gout remedies, e.g. benzbromarone, allopurinol; external dermatological agents, including antibacterial agents, antimycotics, antiviral active substances, anti-inflammatory active substances, antipruritic active substances, anaesthetising active substances, e.g. benzocaine, corticoids, anti-acne agents, antiparasitic active substances; externally applicable hormones; venous therapeutic agents; immunosuppressives etc., all for external application.

Preferred therapeutic agents are analgesics, e.g. immunosuppressives, hormones, agents for the treatment of skin diseases such as neurodermatitis, atopic dermatitis etc., and antiherpes agents.

The skeleton-forming agents, in particular the polysaccharides, may also have certain therapeutic effects (for instance, the skeleton-forming agent that is preferably used, (sodium) alginate, acts antivirally to a certain extent), but they are not active substances in the sense of the invention.

The shaped articles that are used in accordance with the invention optionally contain, moreover, one or more auxiliary substances. Auxiliary substances include: surface-active agents in addition to the aforementioned washing surfactants, such as dispersing agents, emulsifiers etc., fillers, pH-adjusting agents, such as buffering substances, stabilisers, co-solvents, pharmaceutically and cosmetically conventional or other dyestuffs and pigments, preservatives, plasticisers, lubricants and slip additives, etc. Squalane is a particularly preferred auxiliary substance.

The shaped articles according to the invention serve for external application on humans or animals. External application is effected in such a way that the shaped article according to the invention is moistened with water or with an aqueous solution that contains one or more active substances and/or auxiliary substances, or is dissolved in water. Depending on the quantity of liquid and on the solubility of the material of the shaped article that is used, the shaped article may be totally dissolved, forming a solution, or may disintegrate, forming a gel. If the shaped article according to the invention is dissolved in a relatively large quantity of water, it is a question, as a rule, of a bath application, and according to the invention this application is included in external application. However, application is preferably effected in such a way that the shaped articles are moistened with a small quantity of water or of an active-substance and/or auxiliary-substance solution, forming a gel directly on the skin or in the hair, and are rubbed in or massaged in there.

The present invention also relates to a combination including at least one of the shaped articles that are used in accordance with the invention and also at least one aqueous solution that contains one or more active substances and/or auxiliary substances, in a matching spatial arrangement (application pack, set, kit of parts, etc.). In the case of the active-substance solution it may be a question of, for example, solutions of readily volatile active and/or auxiliary substances that, by reason of the production process by freeze drying, should not be or cannot be introduced into the shaped article, such as, for example, certain portions of ethereal oils, perfumes, etc.

Depending on the quantity and type of active substances and/or auxiliary substances that are additionally present, the shaped article that is used in accordance with the invention preferably contains at least approximately 10 wt. % of the skeleton-forming agent, relative to the total weight of the shaped article, preferably at least 15 wt. %, more preferably 30 wt. %, still more preferably at least approximately 50 wt. % up to 100 wt. % of the skeleton-forming agent, especially polysaccharides such as sodium alginate.

The shaped articles generally also contain residues of water. Depending on the type of the active substance (hydrophilic, hydrophobic), the water content may amount to up to 20 wt. %. The water content may change in the course of storage after production of the shaped article by freeze drying; as a rule, it may increase. The water content of the shaped article after production preferably amounts to approximately 2 wt. % to 15 wt. %, more preferably 2 wt. % to 12 wt. %.

The shaped articles that are used in accordance with the invention contain from 0 wt. % to up to 85 wt. %, preferably from 0.000001 wt. % up to 50 wt. %, of one or more active substances. The quantitative ratios depend very much on whether the active substance is a cosmetic active substance or a therapeutic active substance. In particular, the therapeutic active substances find application in very small quantities in certain circumstances.

The shaped articles contain from 0 wt. % to 85 wt. % of one or more auxiliary substances. The shaped articles may contain 0.1 wt. % to 70 wt. % of the auxiliary substances, still more preferably 5 wt. % to 60 wt. % auxiliary substances.

Particularly in the application with an additional active-substance solution, shaped articles can also be applied that consist merely of the hydrophilic skeleton-forming agent and, optionally, additional auxiliary substances.

A preferred auxiliary substance is squalane. In this case it is a question of a cosmetic oil. Despite its hydrophobic nature, the squalane surprisingly brings about an improved solubility of the shaped article, which alleviates external application on the skin. In addition, squalane also has skin-caring effects, even though it is not an active substance in the sense of the invention. In a preferred embodiment the shaped article contains from approximately 10 wt. % to 60 wt. % squalane (determinable by extraction with diethyl ether by the method of Weibull/Stoldt in Amtliche Sammlung von Untersuchungsverfahren ASU in accordance with §35 LMBG).

The classification of the aforementioned substances in the category of the auxiliary substances within the scope of the present invention does not rule out the possibility that these auxiliary substances may also display certain cosmetic and/or therapeutic effects.

A particularly preferred shaped article contains:
at least 10 wt. % of one or more skeleton-forming agents, in particular polysaccharides, such as sodium alginate, in particular calcium-free sodium alginate, the 1 per-cent-by-weight solution or suspension of which in water (1 g in 99 ml water at 20° C., pH 6-8) preferably has a viscosity of less than 2000 mPa.s, preferably less than 1000 mPa.s, particularly preferably less than 100 mPa.s,
0.000001 wt. % up to 50 wt. % of one or more active substances,
0.1 wt. % to 70 wt. % of one or more auxiliary substances, such as, in particular, squalane, and also
up to 20 wt. %, preferably up to 15 wt. %, water, with the proviso that the shaped article does not comprise any proteins by way of skeleton-forming agents.

The shaped article that is used in accordance with the invention, such as, for example, that having the aforementioned composition, containing at least one skeleton-forming agent, proteins being excepted, preferably comprises optionally one or more active substances and also optionally one or more auxiliary substances, for the purpose of external application,
a density from 0.005 g/cm$^3$ up to 0.8 g/cm$^3$, preferably 0.01 g/cm$^3$ up to 0.8 g/cm$^3$,
a volume from 0.1 cm$^3$ to 6 cm$^3$, preferably 0.8 cm$^3$ to 6 cm$^3$, and
a diameter (maximum spacing between two points in the shaped article) of at least 6 mm.

The shaped articles that are used in accordance with the invention constitute porous shaped articles with homogeneous distribution of the constituents (apart from coatings which are optionally present).

The rate. of dissolution of the shaped articles that are used in accordance with the invention, measured in accordance with a method for measuring the "Zerfallszeit von Tabletten und Kapseln" ("Disintegration-time of tablets and capsules") with a test apparatus according to PharmEU, preferably amounts to less than 4 minutes, still more preferably less than 1 minute (in the case of shaped articles with a diameter of 9 mm, complete hydration obtains after <20 seconds without any discernible nucleus).

The shaped articles that are used in accordance with the invention are obtainable by means of a process that comprises the following steps:
(a) producing a solution or suspension that contains at least one biopolymer, optionally one or more physiologically effective active substances and also optionally one or more auxiliary substances,
(b) pouring the solution into a mould,
(c) freezing the solution in the mould and
(d) freeze-drying the frozen solution, forming the shaped article.

In between these steps, further steps may be implemented; in particular, it is possible after step (c) to carry out a treatment of the surface of the shaped articles by machining or by spraying with, for example, active-substance solutions, dyestuff solutions and/or with agents modifying the rate of dissolution. However, the shaped article preferably has no surface coating and is homogeneously structured, in the sense of a uniform distribution of the constituents over the entire shaped article.

The procedure in the course of production is expediently such that, firstly, an aqueous solution of the skeleton-forming agent is produced and, subsequently, optionally one or more active substances or alternatively one or more auxiliary substances are added and mixed.

In order that sufficient mechanical stability can be imparted to the shaped article, it is necessary that the solution or suspension has a certain concentration of the keleton-forming agent. This concentration depends, of course, on the type of the skeleton-forming agent that is used. It expediently amounts to approximately at least 0.1 wt. %, relative to the total quantity of the solution, preferably at least approximately 0.25 wt. % up to approximately 20 wt. %, preferably less than 15 wt. %, still more preferably less than 10 wt. %

(weight of the skeleton-forming agent relative to the total weight of the solution). Higher concentrations are not preferred, because the viscosity of the solution then becomes too high, and as a result the processability of the solution is made more difficult. The quantity of the skeleton-forming agent that is contained in the solution or suspension decisively influences the density (weight of the shaped article relative to the volume of the geometrical shape of the shaped article) of the shaped article that is obtained. The density is, in turn, an important variable for the rate of dissolution of the shaped article in the course of moistening with water or with an active-substance and/or auxiliary-substance solution. The higher the concentration of the skeleton-forming agent in the solution, the higher does the density become (the lower does the degree of porosity become) of the shaped article, and conversely. From the point of view of density or degree of porosity or, to be more exact, the rate of dissolution, the concentration of the skeleton-forming agent in the solution or suspension that is produced in step (a) is preferably selected from a range of approximately 0.25 wt. % to approximately 15 wt. %. The concentration of the skeleton-forming agent that is preferably used, sodium alginate, preferably amounts to from 0.5 wt. % to 5 wt. %, preferably 1 wt. % to 4 wt. %.

The densities of the shaped articles that are used in accordance with the invention expediently amount to approximately 0.01 g/cm$^3$ up to 0.8 g/cm$^3$, preferably approximately 0.015 g/cm$^3$ up to 0.5 g/cm$^3$, preferably approximately 0.02 g/cm$^3$ up to 0.1 g/cm$^3$. The concept of "density" as used in the present document designates the weight of the shaped article relative to the volume of the external geometrical shape of the shaped article.

The weight of the individual shaped articles depends, of course, on the size thereof. In general, the weight of the individual shaped articles amounts to approximately 10 mg to 200 mg, preferably 20 mg to 100 mg. For example, spheres with a diameter of 12 mm have a weight within the range of, preferably, 20 mg to 80 mg, more preferably 30 mg to 60 mg.

For spheres having different diameters, corresponding preferred ranges are calculated.

Production of the solution that is subjected to freeze drying is preferably effected in such a way that, firstly, an aqueous solution of the skeleton-forming agent is produced and, subsequently, the active substances or auxiliary substances which are optionally present are worked into the solution of the skeleton-forming agent. If use is made of oil-soluble active substances, these are preferably dissolved in oils (in particular, squalane) which are optionally used as auxiliary substances, and are subsequently added to the solution of the skeleton-forming agent. This method of production has the advantage that stable solutions or suspensions are formed. No emulsifiers are required, and during the processing no phase separation of the solution or suspension takes place in the case where use is made of oil-soluble or oleaginous auxiliary or active substances.

The solution that has been produced in this way is then poured into a mould that exhibits cavities having the desired geometrical shapes corresponding to the shaped articles. The mould preferably consists of natural rubber, silicone rubber, vulcanised rubber etc. Vulcanised-rubber moulds are preferred. The materials of the mould may optionally be coated. The cavities of the shaped articles into which the solution is poured generally exhibit the shape of the desired shaped article. That is to say, the volume of the cavity corresponds substantially to the volume of the shaped articles that are later obtained.

Since the volume of the solutions or suspensions that have been charged into the cavities increases in the course of freezing (difference in density between water and ice), the cavities are, as a rule, not completely filled. In this way, totally symmetrical shaped articles are obtained. This is, for example, not possible in accordance with the process by instilling into intensely cold solutions (such as into liquid nitrogen), since asymmetrical temperature distributions arise in this process, so that more or less considerable deviations from a regular shape always result. However, precisely in the field of cosmetic end products such irregularly formed shaped articles are not desirable. As a rule, this means that these shaped articles, produced by the instilling process, require aftertreatment, something which is not required with the process as used in accordance with the invention. In the case of the shaped articles that have been produced by the instilling process, such an aftertreatment becomes more and more necessary with increasing volume of the shaped article, since with this process distinct external irregularities arise which become far more visible in the case of larger shaped articles.

After the solution has been charged into the cavities of the mould, the solution or suspension is frozen. Cooling or freezing of the solution can be effected as such in arbitrary manner. Cooling is preferably effected in the process that is used in accordance with the invention by blowing in cold air. Other processes include, for example, the immersion of the moulds in liquid gases, such as, for example, immersion in liquid nitrogen. The rate of cooling influences the size of the ice crystals that are formed. These in turn influence the pore-size distribution of the shaped article that is formed. If few large crystals are formed, the shaped article exhibits few large pores. If many small crystals are formed, the shaped article exhibits many small pores. The crystals become smaller, the higher the rate of cooling of the solution or suspension.

The freezing-temperature that is required depends, inter alia, on how great the lowering of the freezing-point is by virtue of the active substances or auxiliary substances that are contained in the solution. The temperature expediently lies below the freezing-point of water down to the temperature of liquid nitrogen (−196° C.). The freezing-temperature is preferably approximately −20° C. to −80° C. After the freezing of the solution or suspension, the shaped articles are taken out of the mould and optionally subjected to aftertreatment. Aftertreatment can be effected mechanically, for example by means of a surface treatment (grinding, roughening, etc.). Furthermore, a coating treatment is possible, such as, for example, spraying with a salt solution, for example with a view to forming less soluble shapes of the skeleton-forming agents, in particular in the case where use is made of sodium alginate and salt solutions of multivalent metal ions. A dye solution may also be applied superficially onto the frozen shaped articles, resulting in coloured shaped articles.

Subsequently the shaped articles are subjected to freeze drying. Freeze drying can be effected in a manner known as such, as described, for example, in DE 43 28 329 C2 or DE 40 28 622 C2.

The invention will be illustrated in greater detail by the following Examples.

EXAMPLES

Example 1

Sodium-Alginate Sphere, Diameter 12 mm

Basic version with alginate
2 g Protanal LF 10/60 (Na alginate)
98 g water 2 g Na alginate (Protanal LF 10/60) are passed into 98 g water, subject to stirring (2% solution w/w). The homogeneous (degassed) mixture is poured into moulds, frozen out by blowing in air, taken out of the mould and subsequently freeze-dried in a manner known as such. Approximately 110 spheres are obtained.

Example 2

Sphere, Diameter 12 mm

Alginate with squalane
2 g Protanal LF 10/60 (Na alginate)
1 g squalanes
97 g water 2 g Na alginate are passed into 97 g water, subject to stirring, and mixed homogeneously. Subsequently 1 g squalane is added, subject to stirring. The homogeneous (degassed) mixture is poured into moulds, frozen out by blowing in air, taken out of the mould and subsequently freeze-dried in a manner known as such.

Example 3

Sphere, Diameter 9 mm

Alginate with squalane and glycerin
2.0 g Protanal LF 10/60 (Na alginate)
0.9 g squalane
0.6 g glycerin
96.5 g water 2 g Na alginate are dissolved in 96.5 g water, subject to stirring. Subsequently a mixture consisting of 0.9 g squalane and 0.6 g glycerin is added, subject to stirring. The homogeneous (degassed) mixture is poured into moulds, frozen out by blowing in air, taken out of the mould and subsequently freeze-dried in a manner known as such.

Example 4

Sphere, Diameter 12 mm

Alginate with squalane and urea
2.0 g Protanal LF 10/60 (Na alginate)
1.0 g squalane
1.0 g urea
96.0 g water 2 g Na alginate and 1 g urea are dissolved in 96.0 g water, subject to stirring. Subsequently 1.0 g squalane is added, subject to stirring. The homogeneous (degassed) mixture is poured into moulds, frozen out by blowing in air, taken out of the mould and subsequently freeze-dried in a manner known as such.

Example 5

Sphere, Diameter 12 mm

Alginate with squalanes and ceramides
2.0 g Protanal LF 10/60 (Na alginate)
1.5 g squalane
0.01 g ceramide
96.4 g water 2 g Na alginate are dissolved in 96.4 g water, subject to stirring. Subsequently a mixture consisting of 1.5 g squalane and 0.01 g ceramides is added, subject to stirring. The homogeneous (degassed) mixture is poured into moulds, frozen out by blowing in air, taken out of the mould and subsequently freeze-dried in a manner known as such.

The invention claimed is:

1. A method of using a freeze-dried porous shaped article to apply one skeleton-forming agent and optionally one or more selected from the group consisting of cosmetic active substances, pharmaceutical active substances, and auxiliary substances excluding stabilizers and fillers, to an external skin and/or hair surface of a human or an animal, the method comprising:
    step (a): providing a molded, freeze-dried, porous shaped article having the geometrical shape of a sphere with a diameter of at least 5 mm, wherein said shaped article excludes protein-based skeleton-forming agents and comprises:
        (i) one skeleton-forming agent and
        (ii) optionally one or more selected from the group consisting of cosmetic active substances, pharmaceutical active substances, and auxiliary substances;
        wherein the auxiliary substances exclude stabilizers and fillers and are selected from the group consisting of surface-active agents, dispersing agents, emulsifiers, pH-adjusting agents, buffering substances, co-solvents, pharmaceutically and cosmetically conventional dyestuffs, pharmaceutically and cosmetically conventional pigments, preservatives, plasticizers, lubricants and slip additives,
    step (b): contacting the freeze-dried shaped article with
        (i) an aqueous solution comprising water or
        (ii) an aqueous solution that contains at least one selected from the group consisting of active substances and auxiliary substances,
        to form a solution or gel within a dissolution time of less than 4 minutes, measured with a method for measuring the "Disintegration-time of tablets and capsules" with a test apparatus according to PharmEU; and
    step (c): applying the solution or the gel formed in the contacting step to at least one of the external skin and the hair surface of the human or the animal.

2. The method according to claim 1, wherein in step (b) the time of dissolution is less than 1 minute, measured with a method for measuring the "Disintegration-time of tablets and capsules" with a test apparatus according to PharmEU.

3. The method according to claim 1, wherein the skeleton-forming agent is selected from the group of at least partially water-soluble natural polysaccharides or synthetic polymers selected from the group consisting of sodium alginate with a calcium content of less than 3 wt %, natural starches, modified starches, polyacrylic acid, polymethacrylic acid, polymethacrylates PMA, synthetic cellulose derivatives, cellulose ethers, carrageenan, xanthan gum, cellulose, hyaluronic acid and chitosan.

4. The method according to claim 1, wherein the at least one skeleton-forming agent is selected from the group consisting of synthetic cellulose derivatives, cellulose ether, cellulose, hyaluronic acid and sodium alginate having a calcium content of less than 3 wt %.

5. The method according to claim 1, wherein the skeleton-forming agent is selected from the group consisting of synthetic cellulose derivatives, cellulose ether, and hyaluronic acid.

6. The method according to claim 1, wherein in step (a) the porous shaped article comprises one or more active substance selected from the group consisting of
    agents selected from the group consisting of oils that are suitable for cosmetic purposes.

7. The method according to claim 1, wherein at least one cosmetic active substance is present.

8. The method according to claim 1, wherein the porous shaped article further comprises squalane.

9. The method according to claim 1, wherein in step (b) the aqueous solution comprises one or more active substances selected from the group consisting of cosmetic active substances and pharmaceutical active substances.

10. The method according to claim 1, wherein in step (b) the aqueous solution comprises one or more auxiliary substances are selected from the group consisting of surface active agents, dispersing agents, emulsifiers, pH-adjusting agents, buffering substances, co-solvents, pharmaceutically and cosmetically conventional dyestuffs, pharmaceutically and cosmetically conventional pigments, preservatives, plasticizers, lubricants and slip additives.

11. The method according to claim 1, wherein the shaped article according to step (a) exhibits a density within the range of from 0.01 g/cm$^3$ to 0.8 g/cm$^3$ and comprises:
   at least 10 wt. % of the skeleton-forming agents, a 1 percent-by-weight solution or suspension of which in water at 20° C. and at pH 6-8has a viscosity of less than 2000 mPa·s, proteins being excepted,
   0.000001 wt. % up to 50 wt. % of one or more active substances,
   0.1 wt. % to 70 wt. % of the auxiliary substances, and
   up to 20 wt. % water.

12. A method of using a freeze-dried porous shaped article to apply one skeleton-forming agent and one or more selected from the group consisting of cosmetic active substances, pharmaceutical active substances, and auxiliary substances excluding stabilizers and fillers, to an external skin and/or hair surface of a human or an animal, the method comprising:
   step (a): providing a molded, freeze-dried, porous shaped article having the geometrical shape of a sphere with a diameter of at least 5 mm, wherein said shaped article excludes protein-based skeleton-forming agents and comprises:
      (i) one skeleton-forming agent and
      (ii) one or more selected from the group consisting of cosmetic active substances, pharmaceutical active substances, and auxiliary substances;
      wherein the auxiliary substances exclude stabilizers and fillers and are selected from the group consisting of surface-active agents, dispersing agents, emulsifiers, pH-adjusting agents, buffering substances, co-solvents, pharmaceutically and cosmetically conventional dyestuffs, pharmaceutically and cosmetically conventional pigments, preservatives, plasticisers, lubricants and slip additives,
   step (b): contacting the freeze-dried shaped article with
      (i) an aqueous solution comprising water or
      (ii) an aqueous solution that contains at least one selected from the group consisting of active substances and auxiliary substances,
      to form a solution or gel within a dissolution time of less than 4 minutes, measured with a method for measuring the "Disintegration-time of tablets and capsules" with a test apparatus according to PharmEU; and
   step (c): applying the solution or the gel formed in the contacting step to at least one of the external skin and the hair surface of the human or the animal.

13. The method according to claim 12, wherein in step (b) the time of dissolution is less than 1 minute, measured with a method for measuring the "Disintegration-time of tablets and capsules" with a test apparatus according to PharmEU.

14. The method according to claim 12, wherein the skeleton-forming agent is selected from the group of at least partially water-soluble natural polysaccharides or synthetic polymers selected from the group consisting of sodium alginate with a calcium content of less than 3 wt %, natural starches, modified starches, polyacrylic acid, polymethacrylic acid, polymethacrylates PMA, synthetic cellulose derivatives, cellulose ethers, carrageenan, xanthan gum, cellulose, hyaluronic acid and chitosan.

15. The method according to claim 12, wherein the at least one skeleton-forming agent is selected from the group consisting of synthetic cellulose derivatives, cellulose ether, cellulose, hyaluronic acid and sodium alginate having a calcium content of less than 3 wt %.

16. The method according to claim 12, wherein the skeleton-forming agent is selected from the group consisting of synthetic cellulose derivatives, cellulose ether, and hyaluronic acid.

17. The method according to claim 12, wherein in step (a) the porous shaped article comprises one or more active substance selected from the group consisting of
   agents selected from the group consisting of oils that are suitable for cosmetic purposes.

18. The method according to claim 12, wherein at least one cosmetic active substance is present.

19. The method according to claim 12, wherein the porous shaped article further comprises squalane.

20. The method according to claim 12, wherein in step (b) the aqueous solution comprises one or more active substances selected from the group consisting of cosmetic active substances and pharmaceutical active substances.

* * * * *